(12) United States Patent
Russell et al.

(10) Patent No.: US 12,239,523 B2
(45) Date of Patent: *Mar. 4, 2025

(54) CATHETER WITH INTEGRATED EMBOLIC PROTECTION DEVICE

(71) Applicant: Emboline, Inc., Santa Cruz, CA (US)

(72) Inventors: Scott M. Russell, Santa Cruz, CA (US); Amir Belson, Cupertino, CA (US); Stephen J. Kleshinski, Fremont, CA (US); Masao Drexel, Santa Cruz, CA (US)

(73) Assignee: Emboline, Inc., Santa Cruz, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/694,206

(22) Filed: Mar. 14, 2022

(65) Prior Publication Data

US 2022/0265414 A1 Aug. 25, 2022

Related U.S. Application Data

(63) Continuation of application No. 16/790,118, filed on Feb. 13, 2020, now Pat. No. 11,304,792.

(Continued)

(51) Int. Cl.
*A61F 2/01* (2006.01)
*A61F 2/24* (2006.01)
*A61F 2/82* (2013.01)

(52) U.S. Cl.
CPC ............ *A61F 2/013* (2013.01); *A61F 2/2433* (2013.01); *A61F 2002/015* (2013.01); *A61F 2002/016* (2013.01); *A61F 2002/825* (2013.01); *A61F 2210/0014* (2013.01); *A61F 2230/0067* (2013.01); *A61F 2250/0048* (2013.01)

(58) Field of Classification Search
CPC ........ A61F 2/013; A61F 2/014; A61F 2/2436; A61F 2/2433; A61F 2002/015; A61F 2002/016; A61F 2002/825; A61F 2210/0014; A61F 2230/0067;
(Continued)

(56) References Cited

U.S. PATENT DOCUMENTS 4,723,549 A 2/1988 Wholey et al.
4,790,809 A 12/1988 Kuntz
(Continued)

FOREIGN PATENT DOCUMENTS

CA 2575865 A1 1/1998
CA 2609800 A1 1/2007
(Continued)

OTHER PUBLICATIONS

US 6,348,062 B1, 02/2002, Hopkins et al. (withdrawn)
(Continued)

*Primary Examiner* — Jocelin C Tanner
(74) *Attorney, Agent, or Firm* — Shay Glenn LLP

(57) ABSTRACT

A prosthetic heart valve delivery catheter includes an embolic filter to provide integrated embolic protection to inhibit the release of emboli into the aorta, the aortic arch or branch vessels, and other vasculature during transvascular heart valve replacement procedures. The embolic filter will usually be fixedly or movably attached to a shaft of the delivery catheter proximal of the prosthetic heart valve.

5 Claims, 13 Drawing Sheets

Related U.S. Application Data

(60) Provisional application No. 62/844,941, filed on May 8, 2019, provisional application No. 62/804,909, filed on Feb. 13, 2019.

(58) Field of Classification Search
CPC ....... A61F 2250/0048; A61M 25/0068; A61M 25/0082; A61M 2025/0096
See application file for complete search history.

(56) References Cited

U.S. PATENT DOCUMENTS

| | | | |
|---|---|---|---|
| 5,108,419 A | 4/1992 | Reger et al. | |
| 5,197,485 A | 3/1993 | Grooters | |
| 5,554,183 A | 9/1996 | Nazari | |
| 5,643,227 A | 7/1997 | Stevens | |
| 5,769,816 A | 6/1998 | Barbut et al. | |
| 5,769,819 A | 6/1998 | Schwab et al. | |
| 5,797,880 A | 8/1998 | Erskine | |
| 5,800,525 A | 9/1998 | Bachinski et al. | |
| 5,807,327 A | 9/1998 | Green et al. | |
| 5,928,261 A | 7/1999 | Ruiz | |
| 6,013,051 A | 1/2000 | Nelson | |
| 6,083,239 A | 7/2000 | Addis | |
| 6,117,154 A | 9/2000 | Barbut et al. | |
| 6,120,534 A | 9/2000 | Ruiz | |
| 6,139,517 A | 10/2000 | Macoviak et al. | |
| 6,152,144 A | 11/2000 | Lesh et al. | |
| 6,245,012 B1 | 6/2001 | Kleshinski | |
| 6,254,563 B1 | 7/2001 | Macoviak et al. | |
| 6,254,633 B1 | 7/2001 | Pinchuk et al. | |
| 6,258,120 B1 | 7/2001 | McKenzie et al. | |
| 6,348,063 B1 | 2/2002 | Yassour et al. | |
| 6,355,051 B1 | 3/2002 | Sisskind et al. | |
| 6,361,545 B1 | 3/2002 | Macoviak et al. | |
| 6,371,935 B1 | 4/2002 | Macoviak et al. | |
| 6,391,044 B1 * | 5/2002 | Yadav ..................... | A61F 2/013 606/200 |
| 6,461,370 B1 | 10/2002 | Gray et al. | |
| 6,499,487 B1 | 12/2002 | McKenzie et al. | |
| 6,511,496 B1 | 1/2003 | Huter et al. | |
| 6,537,297 B2 * | 3/2003 | Tsugita ................. | A61F 2/0105 606/200 |
| 6,547,760 B1 | 4/2003 | Samson et al. | |
| 6,682,543 B2 | 1/2004 | Barbut et al. | |
| 6,692,513 B2 | 2/2004 | Streeter et al. | |
| 6,695,864 B2 | 2/2004 | Macoviak et al. | |
| 6,709,415 B2 | 3/2004 | Navia et al. | |
| 6,712,834 B2 | 3/2004 | Yassour et al. | |
| 6,746,469 B2 | 6/2004 | Mouw | |
| 6,808,520 B1 | 10/2004 | Fourkas et al. | |
| 7,044,958 B2 | 5/2006 | Douk et al. | |
| 7,229,463 B2 | 6/2007 | Sutton et al. | |
| 7,232,453 B2 | 6/2007 | Shimon | |
| 7,235,060 B2 | 6/2007 | Kraus | |
| 7,537,600 B2 | 5/2009 | Eskuri | |
| 7,758,606 B2 | 7/2010 | Streeter et al. | |
| 7,766,932 B2 | 8/2010 | Melzer et al. | |
| 7,959,662 B2 | 6/2011 | Erbel et al. | |
| 8,052,717 B2 | 11/2011 | Mujkanovic | |
| 8,114,114 B2 | 2/2012 | Belson | |
| 8,123,779 B2 | 2/2012 | Demond et al. | |
| 8,298,258 B2 | 10/2012 | Anderson et al. | |
| 8,308,754 B2 | 11/2012 | Belson | |
| 8,337,519 B2 | 12/2012 | Wasicek | |
| 8,382,788 B2 | 2/2013 | Galdonik et al. | |
| 8,383,788 B2 | 2/2013 | Oliviero | |
| 8,414,482 B2 | 4/2013 | Belson | |
| 8,419,677 B2 | 4/2013 | Ducharme et al. | |
| 8,420,902 B2 | 4/2013 | Gilsinger | |
| 8,430,904 B2 | 4/2013 | Belson | |
| 8,679,149 B2 | 3/2014 | Belson | |
| 8,728,114 B2 | 5/2014 | Belson | |
| 8,740,930 B2 | 6/2014 | Goodwin | |
| 8,968,354 B2 | 3/2015 | Wang et al. | |
| 9,107,734 B2 | 8/2015 | Belson | |
| 9,144,485 B2 | 9/2015 | Bergheim | |
| 9,427,252 B2 | 8/2016 | Sos | |
| 9,492,265 B2 | 11/2016 | Russell et al. | |
| 9,744,023 B2 | 8/2017 | Wang et al. | |
| 9,770,318 B2 | 9/2017 | Belson | |
| 9,827,085 B2 | 11/2017 | Russell et al. | |
| 9,844,387 B2 | 12/2017 | Merchand et al. | |
| 9,877,821 B2 | 1/2018 | Russell et al. | |
| 10,016,267 B2 | 7/2018 | Belson | |
| 10,166,094 B2 | 1/2019 | Russell et al. | |
| 10,617,507 B2 | 4/2020 | Belson | |
| 10,617,509 B2 | 4/2020 | Kleshinski et al. | |
| 10,617,510 B2 | 4/2020 | Russell | |
| 10,736,728 B2 | 8/2020 | Belson | |
| 10,746,280 B2 | 8/2020 | Kamaguchi et al. | |
| 10,870,340 B2 | 12/2020 | Acikgoez et al. | |
| 10,881,494 B2 | 1/2021 | Belson | |
| 10,939,987 B2 | 3/2021 | Belson | |
| 11,051,927 B2 | 7/2021 | Russell et al. | |
| 11,304,792 B2 * | 4/2022 | Russell ................ | A61F 2/2436 |
| 11,399,927 B2 | 8/2022 | Kleshinski et al. | |
| 2001/0044632 A1 | 11/2001 | Daniel et al. | |
| 2002/0004667 A1 | 1/2002 | Adams et al. | |
| 2002/0045916 A1 | 4/2002 | Gray et al. | |
| 2002/0058964 A1 | 5/2002 | Addis | |
| 2002/0111648 A1 * | 8/2002 | Kusleika ............... | A61F 2/0108 606/200 |
| 2002/0128680 A1 | 9/2002 | Pavlovic | |
| 2002/0161394 A1 | 10/2002 | Macoviak et al. | |
| 2003/0040736 A1 | 2/2003 | Stevens et al. | |
| 2003/0040772 A1 | 2/2003 | Hoyodoh et al. | |
| 2003/0100940 A1 | 5/2003 | Yodfat | |
| 2003/0125765 A1 | 7/2003 | Blackledge et al. | |
| 2003/0144686 A1 | 7/2003 | Martinez et al. | |
| 2003/0171803 A1 | 9/2003 | Shimon | |
| 2003/0176884 A1 | 9/2003 | Berrada et al. | |
| 2003/0187474 A1 | 10/2003 | Keegan et al. | |
| 2003/0208223 A1 | 11/2003 | Broome | |
| 2004/0034380 A1 | 2/2004 | Woolfson et al. | |
| 2004/0073253 A1 | 4/2004 | Morrill et al. | |
| 2004/0138692 A1 | 7/2004 | Phung et al. | |
| 2004/0215167 A1 | 10/2004 | Belson | |
| 2004/0225354 A1 | 11/2004 | Allen et al. | |
| 2005/0010246 A1 | 1/2005 | Streeter et al. | |
| 2005/0060017 A1 | 3/2005 | Fischell et al. | |
| 2005/0075724 A1 | 4/2005 | Svanidze et al. | |
| 2005/0137688 A1 | 6/2005 | Salahieh et al. | |
| 2005/0137696 A1 | 6/2005 | Salahieh et al. | |
| 2005/0159773 A1 | 7/2005 | Broome et al. | |
| 2005/0203569 A1 | 9/2005 | Kusleika et al. | |
| 2005/0283186 A1 | 12/2005 | Berrada et al. | |
| 2005/0283231 A1 | 12/2005 | Haug et al. | |
| 2006/0100658 A1 | 5/2006 | Obana et al. | |
| 2006/0129181 A1 | 6/2006 | Callol et al. | |
| 2006/0135977 A1 | 6/2006 | Thompson et al. | |
| 2006/0173490 A1 | 8/2006 | Lafontaine et al. | |
| 2006/0287668 A1 | 12/2006 | Fawzi et al. | |
| 2006/0293706 A1 | 12/2006 | Shimon | |
| 2007/0027534 A1 | 2/2007 | Bergheim et al. | |
| 2007/0060944 A1 | 3/2007 | Boldenow et al. | |
| 2007/0073246 A1 | 3/2007 | Simon | |
| 2007/0073332 A1 | 3/2007 | Miller et al. | |
| 2008/0027481 A1 | 1/2008 | Gilson et al. | |
| 2008/0234722 A1 * | 9/2008 | Bonnette ............... | A61F 2/012 606/200 |
| 2009/0149881 A1 | 6/2009 | Vale et al. | |
| 2009/0254172 A1 | 10/2009 | Grewe | |
| 2010/0010535 A1 | 1/2010 | Mujkanovic | |
| 2010/0106180 A1 | 4/2010 | Strother et al. | |
| 2010/0191326 A1 | 7/2010 | Alkhatib | |
| 2010/0262219 A1 | 10/2010 | Frimerman | |
| 2010/0274277 A1 | 10/2010 | Eaton | |
| 2010/0286768 A1 | 11/2010 | Alkhatib | |
| 2010/0305604 A1 * | 12/2010 | Pah ...................... | A61F 2/011 606/200 |
| 2010/0312268 A1 | 12/2010 | Belson | |
| 2012/0016408 A1 | 1/2012 | Barbut et al. | |
| 2012/0109056 A1 | 5/2012 | Rasmussen | |

(56) References Cited

U.S. PATENT DOCUMENTS

| | | |
|---|---|---|
| 2012/0109182 A1 | 5/2012 | Belson |
| 2012/0172915 A1 | 7/2012 | Fifer et al. |
| 2012/0172918 A1 | 7/2012 | Fifer et al. |
| 2012/0271340 A1 | 10/2012 | Castellano et al. |
| 2012/0271341 A1 | 10/2012 | Hill et al. |
| 2012/0330346 A1 | 12/2012 | Frimerman |
| 2012/0330348 A1 | 12/2012 | Strauss et al. |
| 2013/0035716 A1 | 2/2013 | Belson |
| 2013/0035717 A1 | 2/2013 | Belson |
| 2013/0046330 A1 | 2/2013 | McIntosh et al. |
| 2013/0096606 A1 | 4/2013 | Bruchman et al. |
| 2013/0178891 A1* | 7/2013 | Russell ............... A47C 19/12 606/200 |
| 2013/0245669 A1 | 9/2013 | Basu et al. |
| 2013/0267993 A1 | 10/2013 | Carpenter |
| 2014/0000091 A1 | 1/2014 | Angel et al. |
| 2014/0058372 A1 | 2/2014 | Belson |
| 2014/0214069 A1 | 7/2014 | Franklin |
| 2014/0249568 A1 | 9/2014 | Adams et al. |
| 2014/0277096 A1 | 9/2014 | Richter et al. |
| 2014/0343595 A1 | 11/2014 | Monstadt et al. |
| 2015/0032120 A1 | 1/2015 | Janardhan et al. |
| 2015/0066075 A1 | 3/2015 | Russell et al. |
| 2015/0320540 A1 | 11/2015 | Belson |
| 2015/0342717 A1* | 12/2015 | O'Donnell ............ A61F 2/2439 623/2.11 |
| 2015/0366650 A1 | 12/2015 | Zi et al. |
| 2016/0193045 A1 | 7/2016 | Pollak |
| 2016/0296315 A1* | 10/2016 | Yachia ................... A61F 2/013 |
| 2016/0317276 A1* | 11/2016 | Groh ..................... A61F 2/013 |
| 2016/0317277 A1 | 11/2016 | Carpenter et al. |
| 2016/0367285 A1 | 12/2016 | Sos |
| 2017/0181835 A1 | 6/2017 | Kleshinski et al. |
| 2018/0042390 A1 | 2/2018 | Russell et al. |
| 2018/0206970 A1 | 7/2018 | Eggert et al. |
| 2019/0015152 A1 | 1/2019 | Howard et al. |
| 2020/0054432 A1* | 2/2020 | Martin ................... A61F 2/011 |
| 2020/0281717 A1 | 9/2020 | Spence |
| 2021/0161638 A1 | 6/2021 | Belson |
| 2021/0315680 A1 | 10/2021 | Russell et al. |
| 2022/0008186 A1 | 1/2022 | Belson |
| 2023/0091397 A1 | 3/2023 | Kleshinski et al. |
| 2023/0210650 A1 | 7/2023 | Kleshinski et al. |
| 2023/0293282 A1 | 9/2023 | Kleshinski et al. |
| 2023/0346536 A1 | 11/2023 | Kleshinski et al. |

FOREIGN PATENT DOCUMENTS

| | | | |
|---|---|---|---|
| CN | 1278713 A | | 1/2001 |
| CN | 1331956 A | | 1/2002 |
| CN | 101351242 A | | 1/2009 |
| CN | 201798779 U | | 4/2011 |
| CN | 102186427 A | | 9/2011 |
| CN | 102256566 A | | 11/2011 |
| CN | 102811679 A | | 12/2012 |
| CN | 102973332 A | | 3/2013 |
| CN | 104434263 A | | 3/2015 |
| CN | 105188604 A | | 12/2015 |
| CN | 107072770 A | | 8/2017 |
| CN | 108852555 A | | 11/2018 |
| EP | 1179321 A2 | | 2/2002 |
| JP | H09276414 A | | 10/1997 |
| JP | 2002542879 A | | 12/2002 |
| JP | 2003508114 A | | 3/2003 |
| JP | 2007527264 A | | 9/2007 |
| JP | 2010517622 A | | 5/2010 |
| JP | 4712707 B2 | | 6/2011 |
| WO | WO96/01591 A1 | | 1/1996 |
| WO | WO00/07656 A1 | | 2/2000 |
| WO | WO00/27292 A1 | | 5/2000 |
| WO | WO03/043538 A2 | | 5/2003 |
| WO | WO03/047648 A2 | | 6/2003 |
| WO | WO03/073961 A1 | | 9/2003 |
| WO | WO-03094791 A2 | | 11/2003 |
| WO | WO-2004019817 A1 | | 3/2004 |
| WO | WO-2004021922 A2 | | 3/2004 |
| WO | WO-2006138391 A2 | | 12/2006 |
| WO | WO2008/066881 A1 | | 6/2008 |
| WO | WO-2009038799 A1 | | 3/2009 |
| WO | WO-2013103979 A1 | | 7/2013 |
| WO | WO2015/185870 A1 | | 12/2015 |
| WO | WO-2016040923 A2 | | 3/2016 |
| WO | WO-2016040923 A3 | | 8/2016 |
| WO | WO2017/074530 A1 | | 5/2017 |
| WO | WO2017016828 | | 7/2017 |
| WO | WO2019/089821 A1 | | 5/2019 |
| WO | WO-2020168091 A1 | | 8/2020 |
| WO | WO2021/087480 A1 | | 5/2021 |

OTHER PUBLICATIONS

International Search Report and Written Opinion for PCT/US2020/018128 on May 11, 2020.

U.S. Appl. No. 16/790,118 Office Action dated May 13, 2021.

U.S. Appl. No. 16/790,118 Notice of Allowance dated Dec. 10, 2021.

EP20755499.9 Extended Search Report dated Oct. 11, 2022.

Russell et al.; U.S. Appl. No. 18/658,983 entitled "Integrated embolic protection devices," filed May 8, 2024.

* cited by examiner

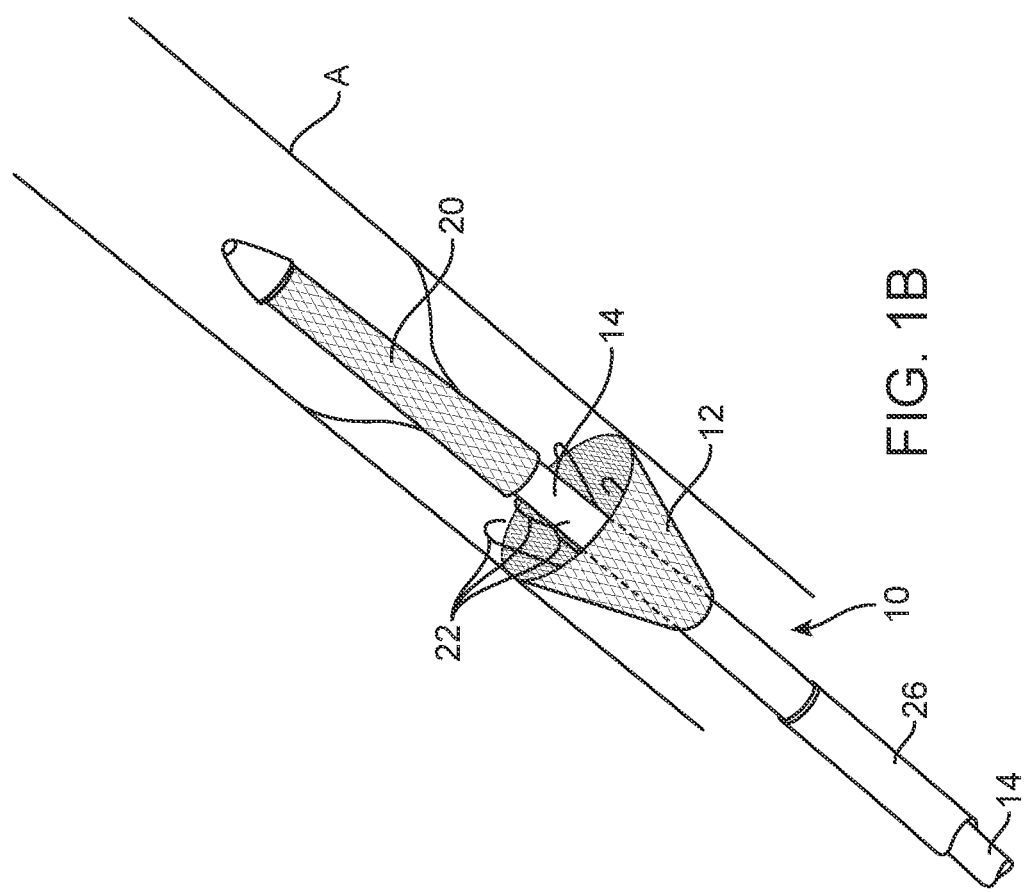
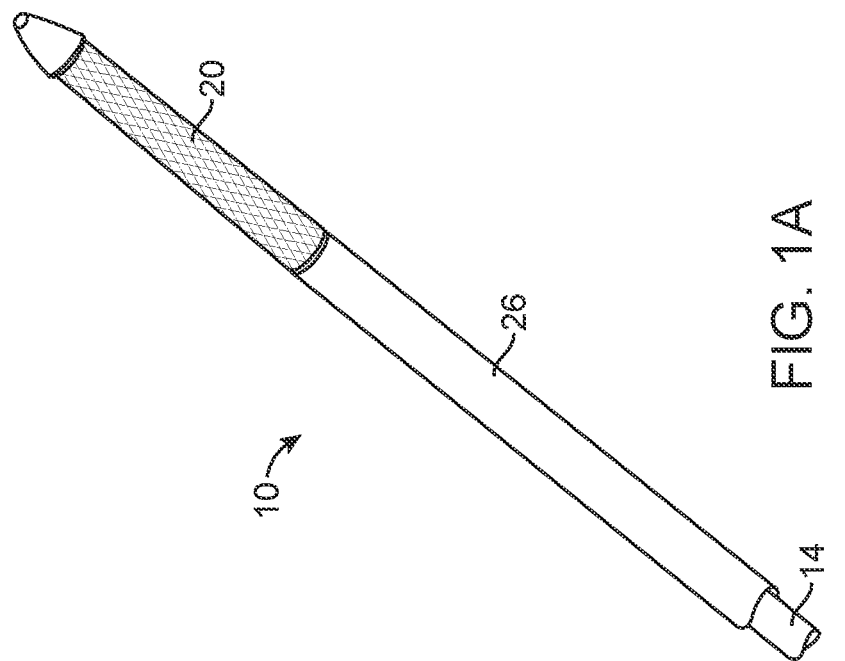

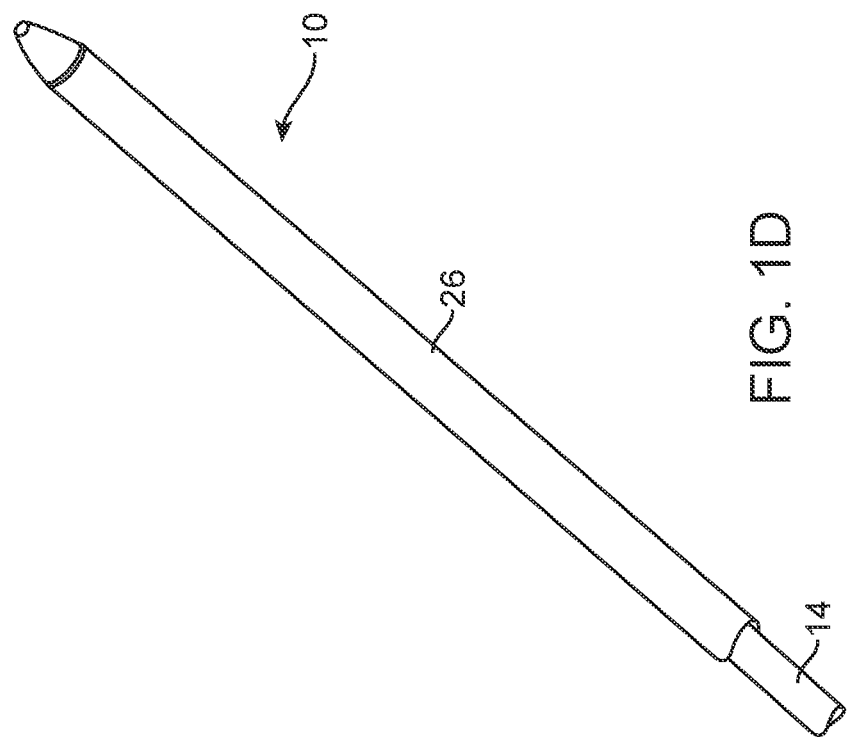
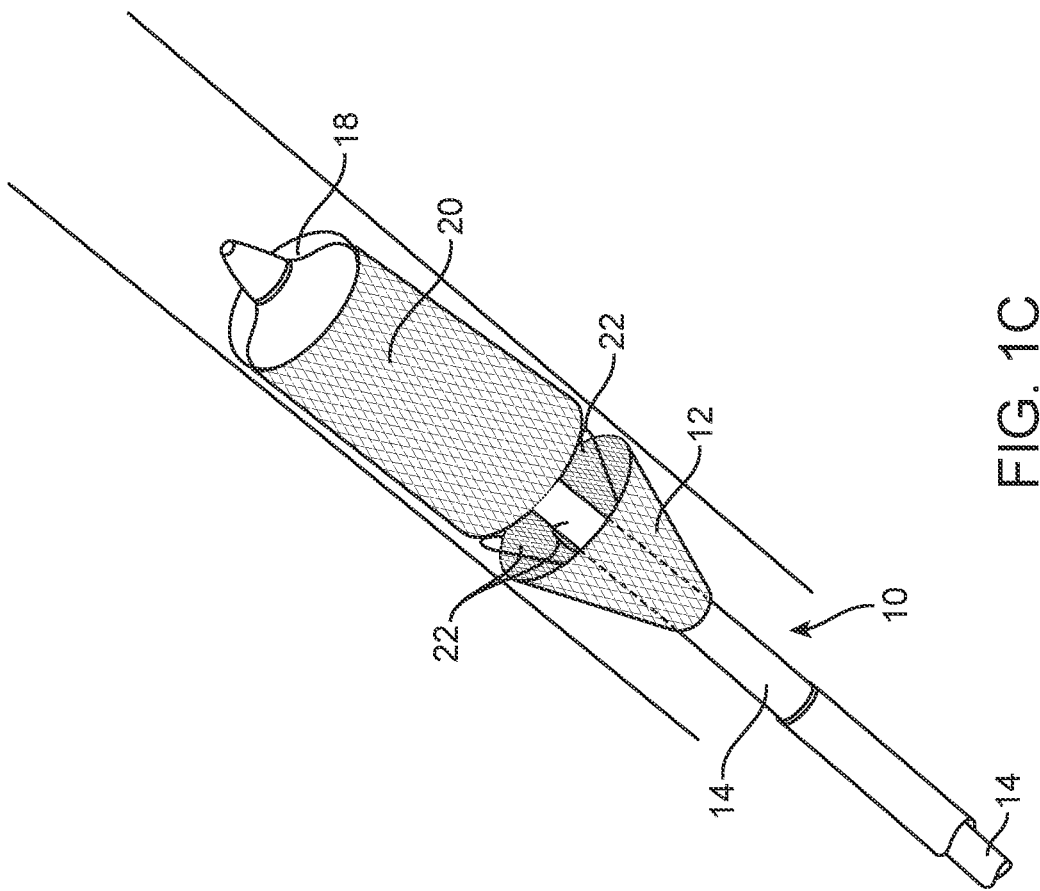

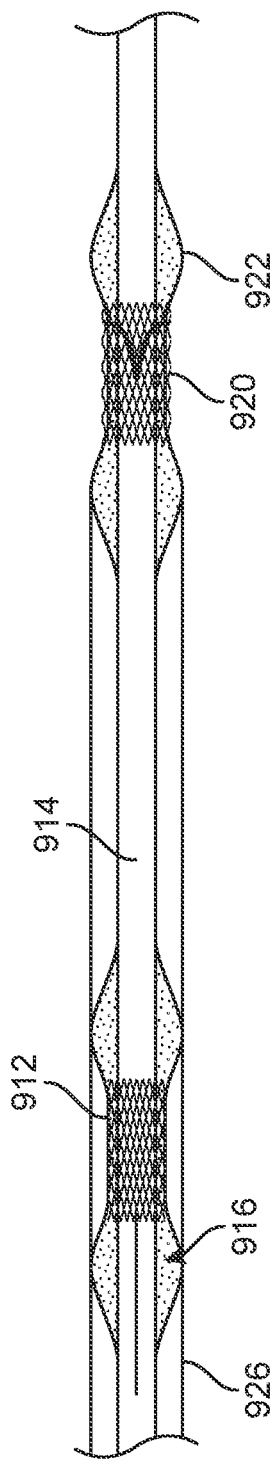
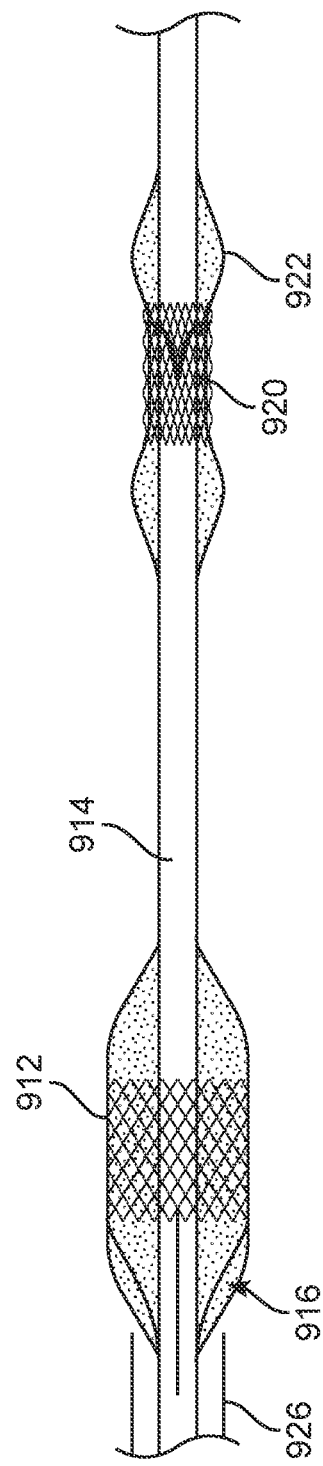
FIG. 9A
FIG. 9B

CATHETER WITH INTEGRATED EMBOLIC PROTECTION DEVICE

CROSS-REFERENCE TO RELATED APPLICATIONS

This application is a continuation of U.S. patent application Ser. No. 16/790,118, filed Feb. 13, 2020, which claims the benefit of prior provisional patent applications Ser. No. 62/844,941, filed on May 8, 2019, and Ser. No. 62/804,909, filed on Feb. 13, 2019, the full disclosures of which are incorporated herein by reference.

BACKGROUND OF THE INVENTION

1. Field of the Invention

The present invention relates to apparatus and methods for providing embolic protection in a patient's vascular system. In particular, it relates to catheters intended for transcatheter heart valve delivery and other intravascular interventional procedures which incorporate an embolic filter.

Cerebral embolism is a known complication of cardiac surgery, cardiopulmonary bypass and catheter-based interventional cardiology and electrophysiology procedures. Embolic particles, which may include thrombus, atheroma and lipids, may become dislodged by surgical or catheter manipulations and enter the bloodstream, embolizing in the brain or other vital organs downstream. Cerebral embolism can lead to neuropsychological deficits, stroke and even death. Other organs downstream can also be damaged by embolism, resulting in diminished function or organ failure.

Prevention of embolism would benefit patients and improve the outcome of these procedures. Given that potential emboli are often dislodged during catheter-based procedures, it would be advantageous to deploy an embolic protection system as part of a catheter-based vascular procedure, such as transcatheter aortic valve replacement (TAVR). Further, the use of transcranial doppler (TCD) during TAVR has shown that cerebral emboli are generated primarily during the procedural steps of crossing the native valve and deploying the TAVR valve (Reference Kahlert, et al, *Circulation,* 2012). Therefore, the integration of an embolic protection device on the TAVR delivery system itself would have the advantage that the protection is in place for the most critical steps of the procedure. Another advantage would come by integrating the embolic protection system on the catheter itself that is being used to perform the procedure, such as a transcatheter valve delivery system or electrophysiology catheter. Other embolic protection systems require separate procedural steps for installing the protector prior to the interventional or diagnostic procedure and removing it after the procedure. In many cases a different access site is required as well. The present invention avoids both the extra step and the need for an extra access site. Yet another advantage would come from providing an integrated embolic protection device that does not increase the overall diameter of the catheter.

2. Description of the Background Art

Devices for preventing embolisms and similar events are described in the following patents and patent applications, which are hereby incorporated by reference: U.S. Pat. Nos. 10,166,094; 9,877,821; 9,744,023; 9,144,485; 8,968,354; 8,740,930; 8,420,902; 8,383,788; 8,337,519; 8,123,779; 8,052,717; 7,537,600; 7,044,958; 6,537,297; 6,499,487; 6,371,935; 6,361,545; 6,254,563; 6,139,517; 5,769,816; U.S. Pat. App. 2019/0015152; U.S. Pat. App. 2018/0206970; U.S. Pat. App. 2018/0042390; U.S. Pat. App. 2016/0317277; U.S. Pat. App. 2015/0366650; U.S. Pat. App. 2014/0214069; U.S. Pat. App. 2013/267993; U.S. Pat. App. 2012/271340; U.S. Pat. App. 2010/0312268; U.S. Pat. App. 2010/0010535; U.S. Pat. App. 2004/0215167; U.S. Pat. App. 2003/0100940; and PCT App. WO2004/019817.

SUMMARY OF THE INVENTION

A prosthetic heart valve delivery catheter having integrated embolic protection according to the principles of the present invention inhibits the release of emboli into the aorta, the aortic arch or branch vessels, and other vasculature to protect the brain and other downstream organs from embolization during transvascular prosthetic heart valve replacement procedures. Unlike most other embolic protection solutions, the embolic filter is integrated into an interventional or diagnostic catheter, such as a transcatheter heart valve delivery system.

In a first aspect, the present invention provides a prosthetic heart valve delivery catheter system having integrated embolic protection. The catheter system typically comprises a catheter shaft having a distal portion, a prosthetic valve disposed on the distal portion of the catheter shaft; and an embolic filter disposed on the distal portion of the shaft at a location proximal of the prosthetic valve. The embolic filter has a collapsed configuration and a deployed configuration, and an outer periphery of the filter is configured to contact a blood vessel wall in the expanded configuration. In some embodiments, the embolic filter comprises a filter structure having a narrow end coupled to the shaft and an open end located distally of the narrow end.

In specific embodiments, the narrow end of the filter structure may fixedly attached to the catheter shaft. In alternative embodiments, the narrow end of the filter structure is slidably mounted on the catheter shaft. The catheter may further comprise at least one of a proximal stop on the catheter shaft for limiting proximal movement of the embolic filter on the distal portion of the catheter shaft and a distal stop on the catheter shaft for limiting distal movement of the embolic filter on the distal portion of the catheter shaft.

In further specific embodiments, the filter may comprise a filter membrane and a support structure. The support structure may comprise a plurality of self-expanding axial struts connected at their proximal ends to the catheter shaft so as to open a distal end of the filter member to form a cone when released from constraint. The axial struts may have atraumatic distal tips.

In other embodiments, the filter may comprise a self-expanding conical filter. For example, the embolic filter comprises a porous material comprising a fabric of knitted, woven, or nonwoven fibers, filaments, or wires. The porous material may be made of a resilient metal, polymer material, a malleable material, a plastically deformable material, a shape-memory material, or combinations thereof. The porous material will typically have a pore size chosen to prevent emboli over a predetermined size from passing through.

In a second aspect, the present invention provides systems comprising a catheter as described above in combination with an outer delivery sheath configured to maintain the embolic filter in a collapsed configuration.

In a third aspect, the present invention provides a prosthetic heart valve delivery catheter having integrated embolic protection. The prosthetic heart valve delivery catheter typically comprises a catheter shaft having a distal portion, a prosthetic valve disposed on the distal portion of the catheter shaft; and an embolic filter disposed on the distal portion of the shaft at a location proximal of the prosthetic valve. The embolic filter will usually have a collapsed configuration and a deployed configuration and, in the expanded configuration, an outer periphery of the filter contacts a blood vessel wall The embolic filter will typically comprise a filter membrane and a support structure, wherein the support structure comprises a cage having a distal collar and a proximal collar attached to the distal portion of the catheter shaft.

In specific embodiments, at least one of the distal collar and the proximal collar is slidably attached to the distal portion of the catheter shaft. In other embodiments, at least one of the distal collar and the proximal collar is fixedly attached to the distal portion of the catheter shaft. For example, at least one of the distal collar and the proximal collar is fixedly attached to the distal portion of the catheter shaft. In other examples, at least one of the distal collar and the proximal collar is configured to be axially translated to expand and contract the cage. Typically, the cage is self-expanding so that it can be radially constrained for delivery and released from radial constraint for deployment. In still further examples, the cage has a conically tapered distal end, a conically tapered proximal end, and a cylindrical wall portion therebetween, wherein the filter membrane covers at least the conically tapered proximal end and does not cover the conically tapered distal end.

In a fourth aspect, the present invention provides a prosthetic heart valve delivery catheter having integrated embolic protection. The catheter comprises a catheter shaft having a distal portion, a prosthetic valve disposed on the distal portion of the catheter shaft, and an embolic filter disposed on the distal portion of the shaft at a location proximal of the prosthetic valve. The embolic filter typically has a collapsed configuration and a deployed configuration where an outer periphery of the filter is configured to contact a blood vessel wall. The embolic filter usually further comprises a cylindrical wall portion located proximal of the prosthetic valve and configured to cover a patient's aortic branch vessels and a conical wall portion proximal of the cylindrical wall portion.

In specific embodiments, a cylindrical wall portion and a conical wall portion are not continuous. For example, at least one of cylindrical wall portion and the conical wall portion may be fixedly attached to the distal portion of the catheter shaft. In other examples, at least one of cylindrical wall portion and the conical wall portion is slidably attached to the distal portion of the catheter shaft. In still other examples, at least one of cylindrical wall portion and the conical wall portion is self-expanding. In any of these examples, at least one of cylindrical wall portion and the conical wall portion is balloon expandable.

In a fifth aspect, the present invention provides a prosthetic heart valve delivery catheter having integrated embolic protection, where catheter comprises a catheter shaft having a distal portion, a prosthetic valve disposed on the distal portion of the catheter shaft, and an embolic filter disposed on the distal portion of the shaft at a location proximal of the prosthetic valve. The embolic filter typically has a collapsed configuration and a deployed configuration where an outer periphery of the filter is configured to contact a blood vessel wall. The embolic filter will usually further comprise a cylindrical wall having an open distal end and a closed proximal end sealing coupled to the catheter shaft, where a proximal region of the cylindrical wall is movably everted and allows the open distal end to axially translate relative to the catheter shaft while the closed proximal end remains stationary relative to the catheter shaft.

In specific embodiments, the closed proximal end is fixed to the catheter shaft. For example, the closed proximal end may slidably couple to the catheter shaft. At least the distal portion of the cylindrical wall may be self-expanding and at least at the distal portion of the cylindrical wall may comprise a self-expanding filter.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1A-1D shows a first embodiment of a valve delivery system according to the present invention with a balloon-deployable prosthetic cardiac valve having integrated embolic protection.

FIGS. 9A-9D show an eighth embodiment of a valve delivery system according to the present invention similar to the valve delivery system of FIG. 1.

DETAILED DESCRIPTION OF THE INVENTION

Figure 2A:
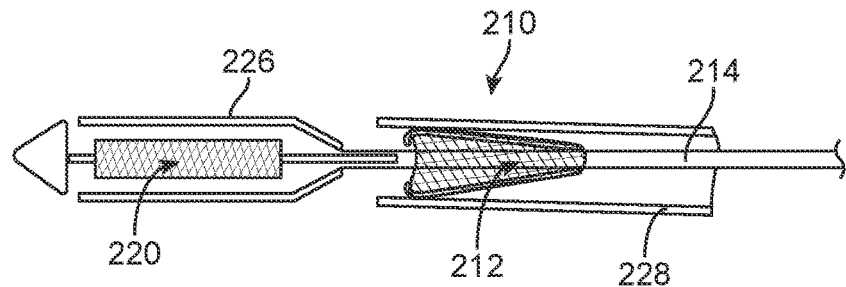
FIGS. 2A-2D shows a second embodiment of a valve delivery system according to the present invention with a self-expanding prosthetic cardiac valve having integrated embolic protection.

For purposes of this patent application, the term "distal" refers to the end of the device that is farthest away from the operator, and closest to the heart. This is also the "upstream" direction of blood flow. The term "proximal" refers to the end of the device nearer to the operator, toward the direction of the access site where the device has been introduced into the body, and farthest away from the heart. This is also the "downstream" direction of blood flow.

FIGS. 1A-1D show an integrated valve system 10 having integrated embolic protection according to the present invention. A self-expanding, conical embolic filter 12 is mounted on a shaft 14 of a balloon valve delivery catheter having a balloon-expandable prosthetic cardiac valve 20 mounted on a distal balloon 18. The balloon-expandable aortic valve may be any one of a variety of available and proposed balloon expandable cardiac valves, such as an Edwards Sapien® valve. The conical embolic filter 12 may be mounted on the catheter shaft 14 with either a fixed attachment or a sliding attachment. A fixed attachment simplifies both construction and the deployment protocol but limits the ability to adjustably position the conical filter relative to the aortic valve during delivery. When fixedly attached, the distal end of the conical filter may be positioned from 1 cm to 20 cm proximal of the proximal end of the prosthetic valve 20, typically being from 1 cm to 10 cm proximal of the proximal end of the prosthetic valve. When slidably attached, the distal end of the conical filter may be adjusted (before or during deployment) to be positioned from 1 cm to 30 cm proximal of the proximal end of the prosthetic valve 20, typically being from 1 cm to 20 cm proximal of the proximal end of the prosthetic valve.

The self-expanding, conical embolic filter 12 typically comprises a mesh or other filter material having a mesh size suitable for embolic capture and a self-expanding support structure, such as a plurality of radially self-expanding struts 22 to ensure full expansion of the mesh or other filter material. As illustrated, the radially self-expanding struts 22 have atraumatic distal tips to contact the aortic wall, e.g. distal ends of the struts may be curved, coiled, have protective pads, or have other structures to inhibit tissue injury.

The self-expanding, conical embolic filter 12 is typically deployed by retracting a constraining sheath 26 (compare FIGS. 1A and 1B) and may be collapsed by advancing the constraining sheath and/or retracting the catheter shaft 14 (compare FIGS. 1C and 1D). Optionally, after deployment of the valve 20, the constraining sheath may be used to cover the deflated balloon 18 as well as the conical filter (FIG. 1D).

FIGS. 2A-2D shows a second embodiment of a valve system 210 having integrated embolic filter 212 on a catheter shaft 214 according to the present invention. The integrated valve system 210 is adapted to deliver a self-expanding prosthetic valve 220, such as a Medtronic CoreValve® heart valve mounted on a distal end of the catheter shaft 214. The self-expanding prosthetic valve 220 is initially constrained for delivery by a first retractable constraining sheath 226, and the embolic filter 212 is initially constrained for delivery by a second retractable sheath 228.

Figure 2B:
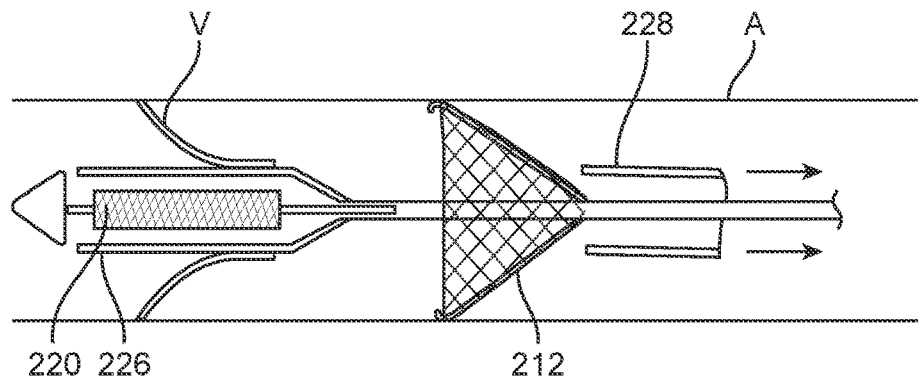
Figure 2C:
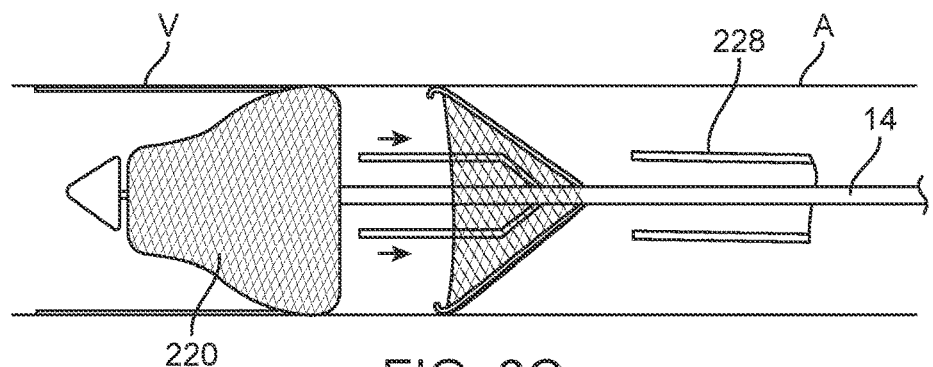
Figure 2D:
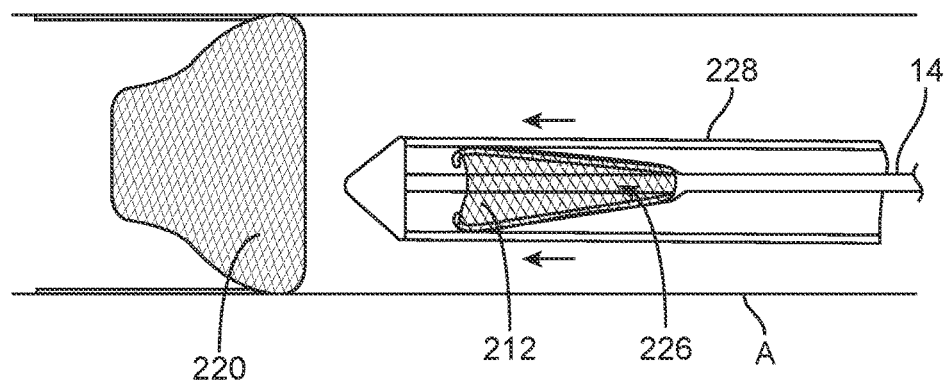

After positioning the first constraining sheath 226 and prosthetic valve 220 in the aortic valve V, the filter 212 is deployed by retraction of the second sheath 228, allowing the filter to expand (FIG. 2B). The prosthetic valve 220 is then deployed by retraction of second retractable sheath 228 (FIG. 2C). After valve deployment, the second retractable sheath 228 is advanced to collapse the filter 212 and first sheath 226 for removal of the system. As shown in FIG. 2D, the first containing sheath 226 may be collapsed within the collapsed filter 212 which in turn is collapsed in the second constraining sheath 228. Alternatively, the first retractable constraining sheath 226 could be advanced prior to the collapse of the filter 212 by advancement of the second retractable sheath 228. In this alternative, the first constraining sheath 226 would lie distal to the second retractable sheath 228 as the catheter shaft 14 is withdrawn from the aorta.

Figure 3:
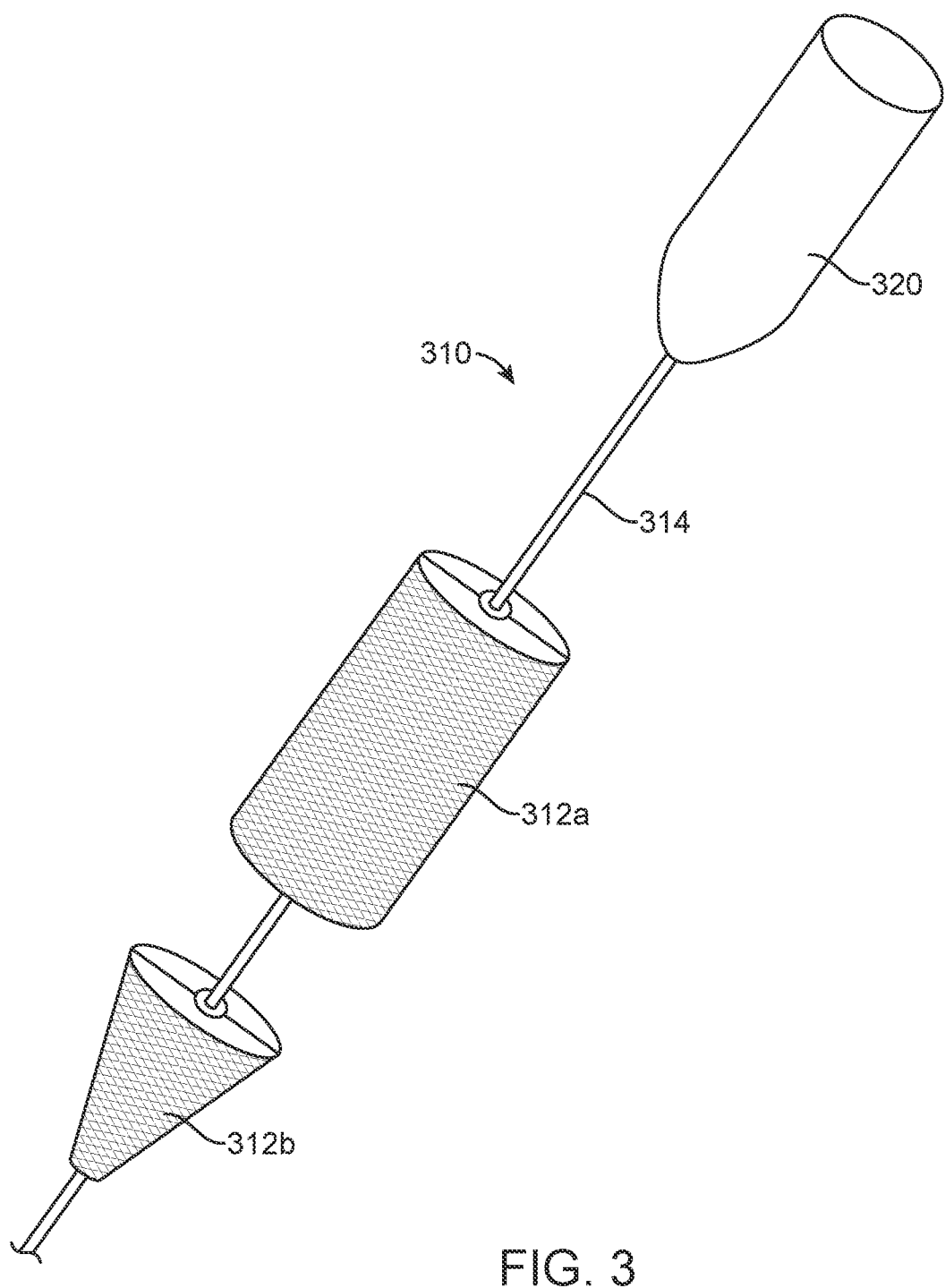
FIG. 3 shows a third embodiment of a valve delivery system according to the present invention with an integrated embolic protection including both an emboli deflector element and a separate emboli capture element.
Figure 4:
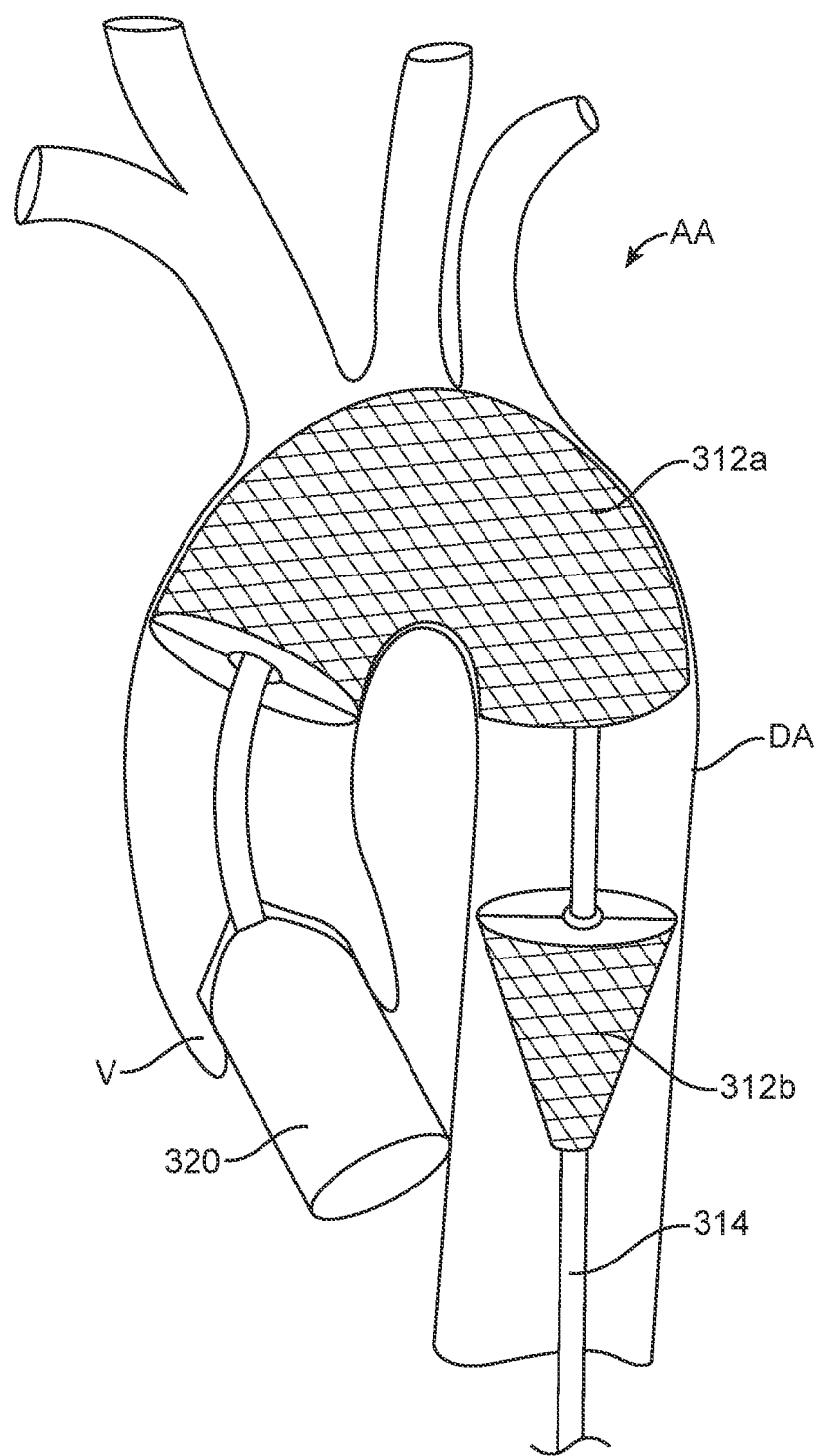
FIG. 4 illustrates the valve delivery system if FIG. 3 deployed in an aortic arc with a prosthetic aortic valve being implanted in a native aortic valve.

FIGS. 3 and 4 show a third embodiment of a valve system 310 having an integrated embolic filter assembly 312 on a catheter shaft 314 according to the present invention. The embolic filter assembly comprises a distal cylindrical or panel-shaped deflector 312a (as described for example in U.S. Pat. No. 8,114,114, the full disclosure of which is incorporated herein by reference) that is deployed across the great vessels of the aortic arch AA and a separate conical or other capture basket 312b that sits downstream or proximal of the deflector 312a in the descending aorta DA, as shown in FIG. 4. The valve system 310 will include a prosthetic valve 320 which may be positioned and deployed in the patient's aortic valve V using either the balloon expandable or the self-expanding protocols described previously.

Figure 5A:
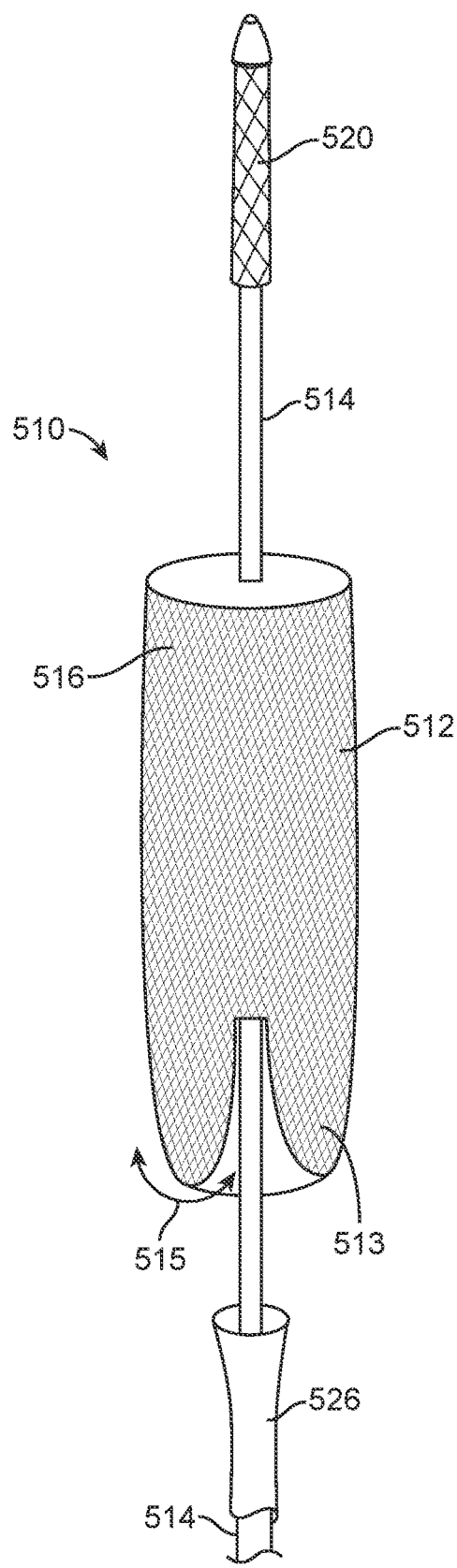
FIGS. 5A-5D show a fourth embodiment of a valve delivery system according to the present invention having an elongated cylindrical filter mesh deployed over an aortic arch while delivering a prosthetic aortic valve in a native aortic valve.
Figure 5B:
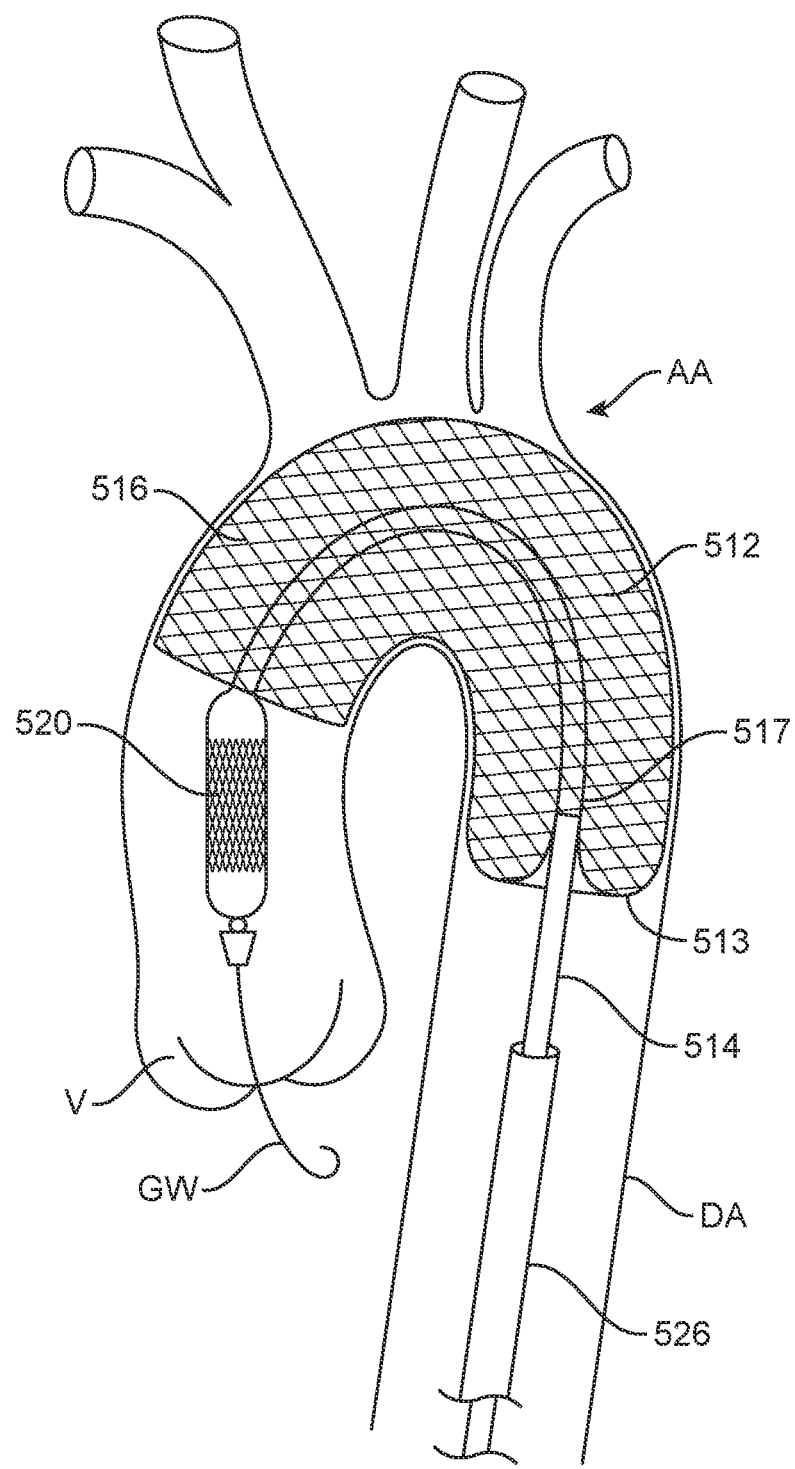
Figure 5C:
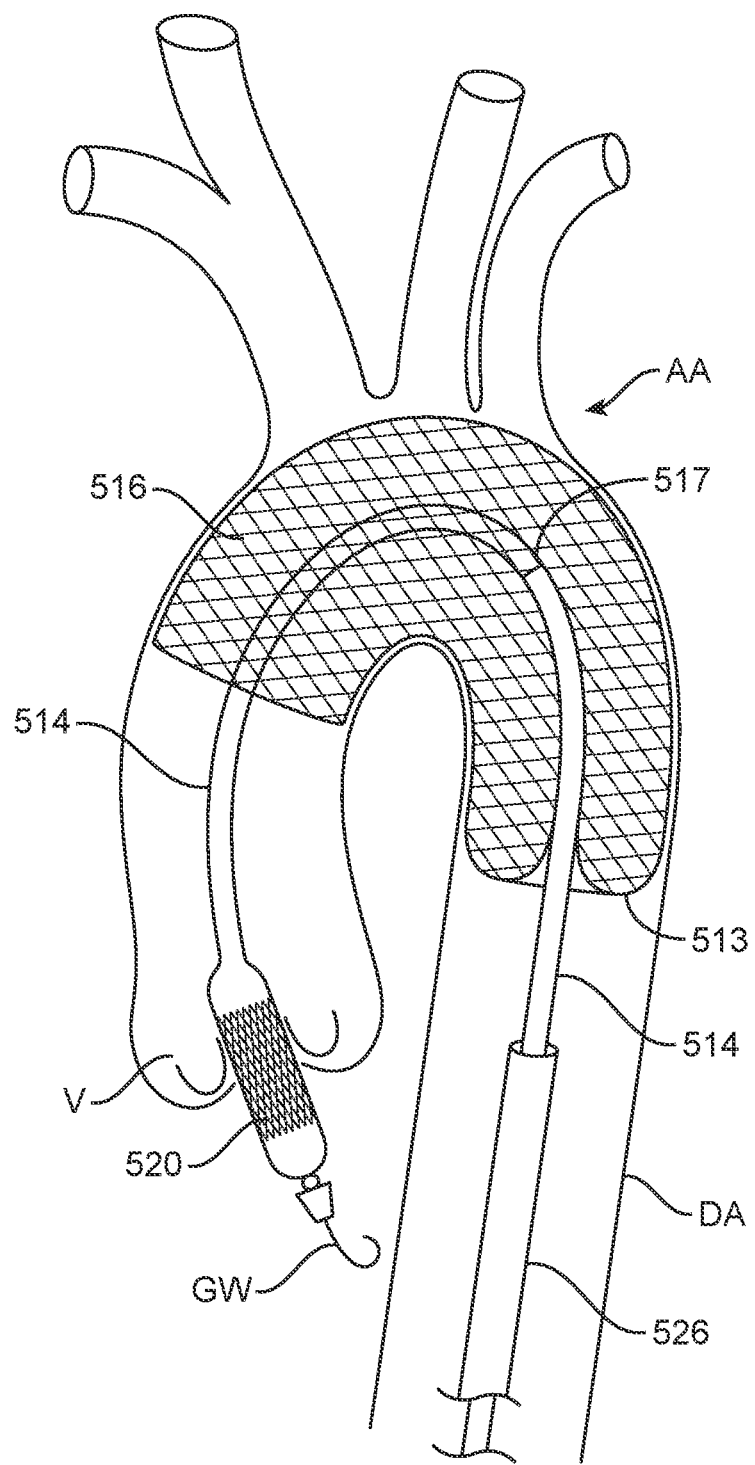
Figure 5D:
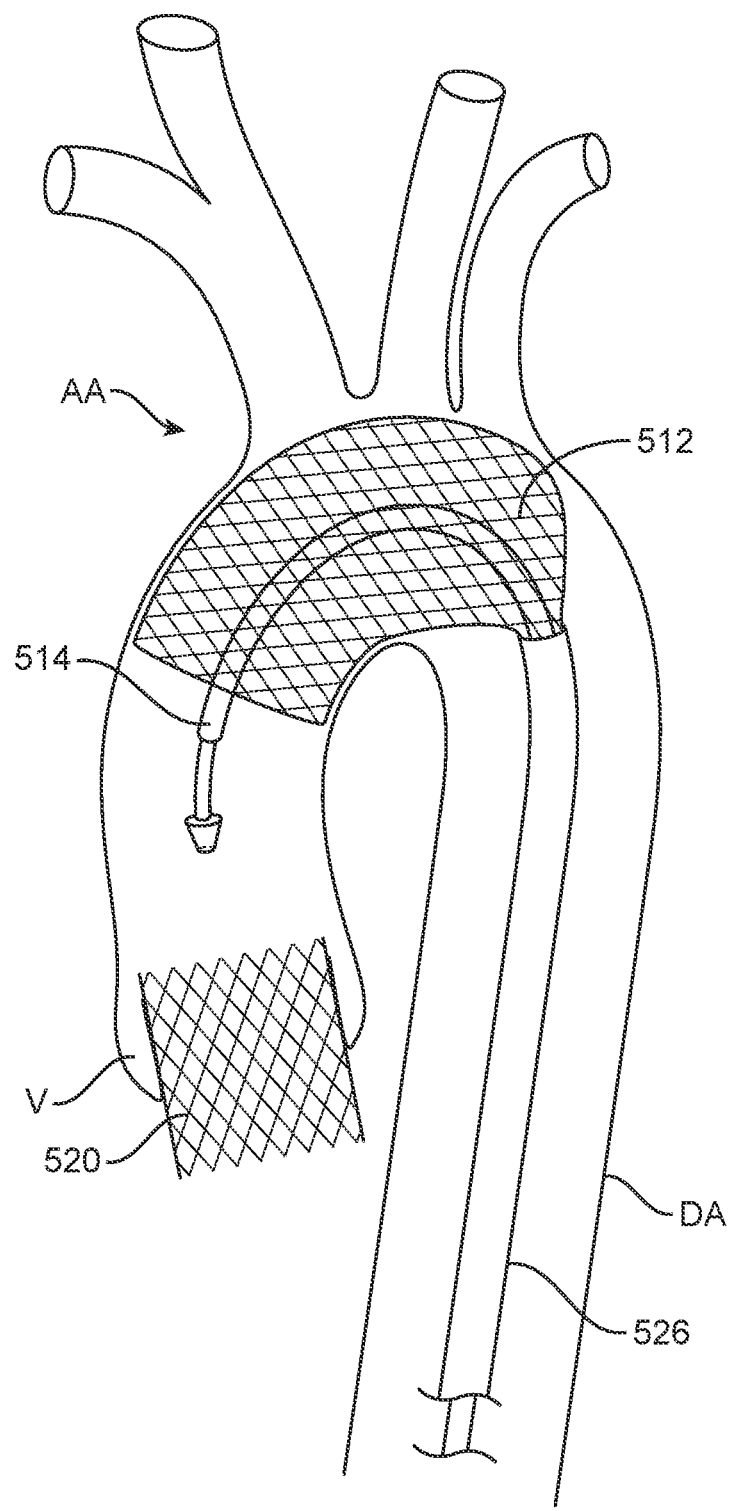

FIG. 5A shows a fourth embodiment of a valve system 510 having an integrated embolic filter in accordance with of the principles of the present invention. A proximal portion 513 everts to form a flexible section that can be reversibly "rolled" to accommodate bidirectional axial movement of the catheter shaft 514 without while leaving a distal portion 516 of the embolic filter stationary against the vessel wall. This allows a proximal end of the embolic filter, which is fixed to the delivery catheter at an attachment junction 517, to move with the catheter shaft 514 as the catheter is advanced and retracted to position the valve for delivery without requiring the distal filter portion move and slide along the vessel wall as the catheter is advanced and retracted. Compare FIG. 5B which shows the filter 512 deployed in the aortic arch AA prior to deployment of the prosthetic aortic valve 520 and FIG. 5C which shows the filter 512 after the prosthetic valve 520 has been advanced into its deployment position within the native valve V. Note that the attachment junction 517 of the proximal end of the embolic filter 512 has advanced forward to allow the prosthetic valve 512 to be advanced into position without moving the main body of the embolic filter where it covers the cerebral branch vessels of the aortic arch AA. After deployment of the valve 512, the filter may be retracted back into the deployment sheath 526, as shown in FIG. 5D.

Figure 6:
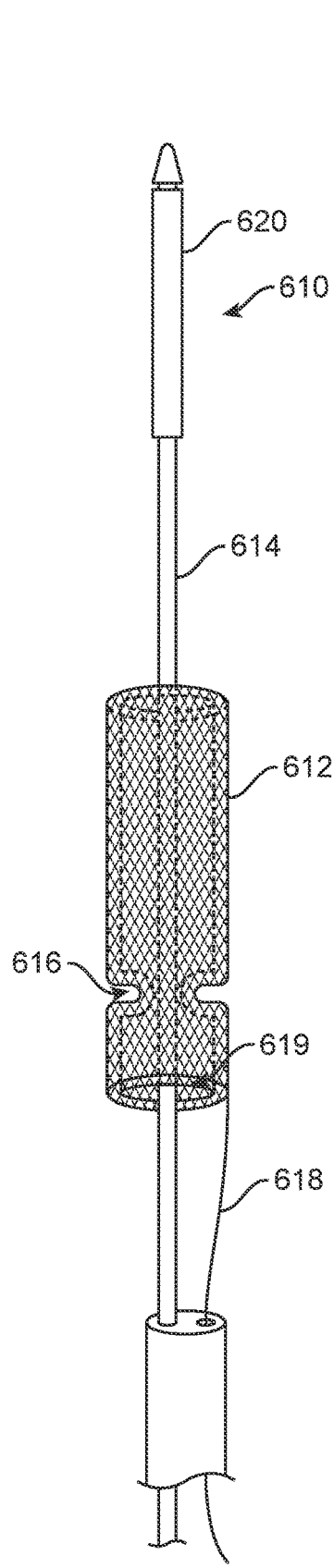
FIG. 6 shows a fifth embodiment of a valve delivery system according to the present invention having an embolic filter that is mounted around the valve system catheter during initial delivery.

FIG. 6 shows a fifth embodiment of an embolic filter 612 in accordance with the present invention where the filter is mounted around a shaft 614 of a valve system 610 catheter during initial delivery. After deployment of the filter 612, the shaft 614 can move freely through an access port 616 that accommodates the catheter while inhibiting embolic debris release. The filter 612 is held in position and recovered with a tether 618 that connects to a proximal end of the filter. The tether 618 can be rigid to allow both proximal and distal repositioning, as well as retrieval. Retrieval can be accomplished by pulling the filter into a separate lumen of the delivery system (not shown). The filter can be collapsed for retrieval via a mechanism such as a "purse string" loop 619 (shown) or elongation of a support frame.

Figure 7:
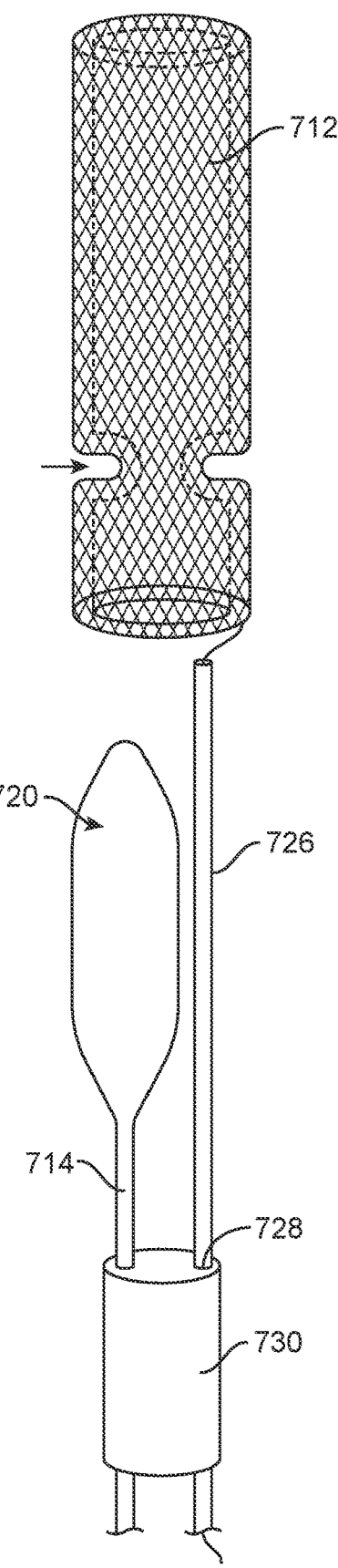
FIG. 7 shows a sixth embodiment of a valve delivery system according to the present invention having a prosthetic valve and embolic filter similar to those of FIG. 6 where a filter delivery sheath is deployed and retrieved via a separate catheter in a separate lumen of the valve delivery catheter located adjacent to the catheter that contains the prosthetic valve.

FIG. 7 shows a sixth embodiment of an embolic filter 712 in accordance with the present invention in which a filter delivery sheath 726 is deployed and retrieved via a separate lumen 728 in a valve delivery catheter 730. The valve delivery catheter 730 also has a lumen for a valve delivery shaft 714 which carries prosthetic valve 720. Upon deployment of the embolic filter 712, the prosthetic valve 720 can be advanced through the embolic filter and to the valve implantation site. The filter catheter 726 can be independently advanced and retracted so that it can be advanced ahead of the valve catheter 714 for deployment and positioning of the filter 720, and then withdrawn while the valve catheter is advanced past the filter catheter and through the access port of the filter mesh or other filter material. After valve deployment, the valve catheter 714 can be withdrawn and the filter catheter 726 advanced to assist in retrieval of the filter mesh or other filter material.

Figure 8:
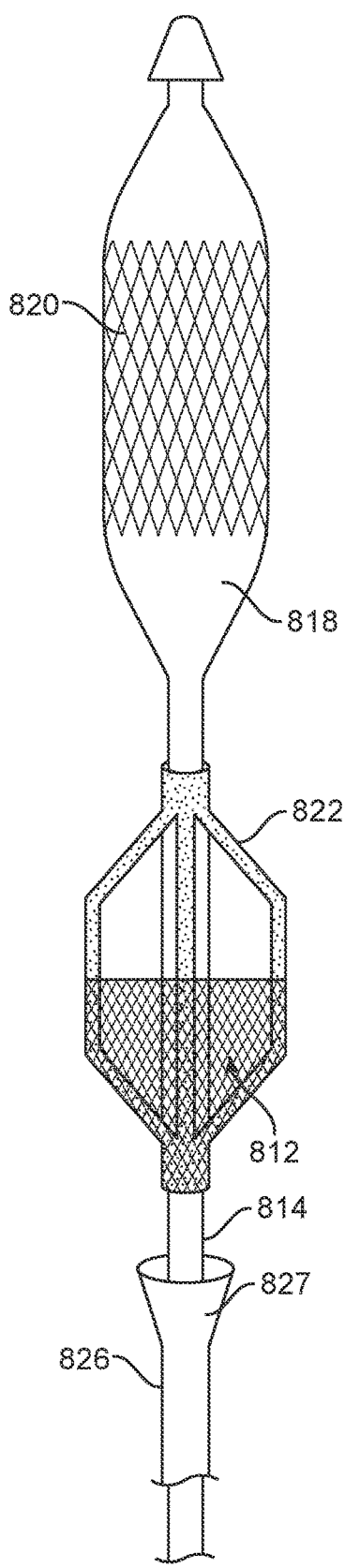
FIG. 8 shows a seventh embodiment of a valve delivery system according to the present invention having an embolic filter mounted on a valve delivery system with both ends of a support structure attached to the delivery catheter.

FIG. 8 shows a seventh embodiment of an embolic filter 812 in accordance with the present invention where the embolic filter is mounted with both ends of a filter support structure 822, such as self-expanding cage, attached to a delivery catheter 814. The embolic filter 812 is open (free from the filter mesh) on its distal end and closed on its proximal direction for debris capture when deployed. At least one of the proximal end or distal end of the filter support structure 822 is slidably attached to the delivery catheter 814 to allow radial opening and collapse. In some instances, both the distal and proximal ends on the support structure 822 will be slidably attached to catheter 814 to allow the balloon 818 and valve 820 to be positioned after the filter 812 is deployed.
A conical guiding structure 827 ("funnel") at the end of the constraining sheath 826 assists in deployment and retrieval of the filter and support structure.

Figure 9C:
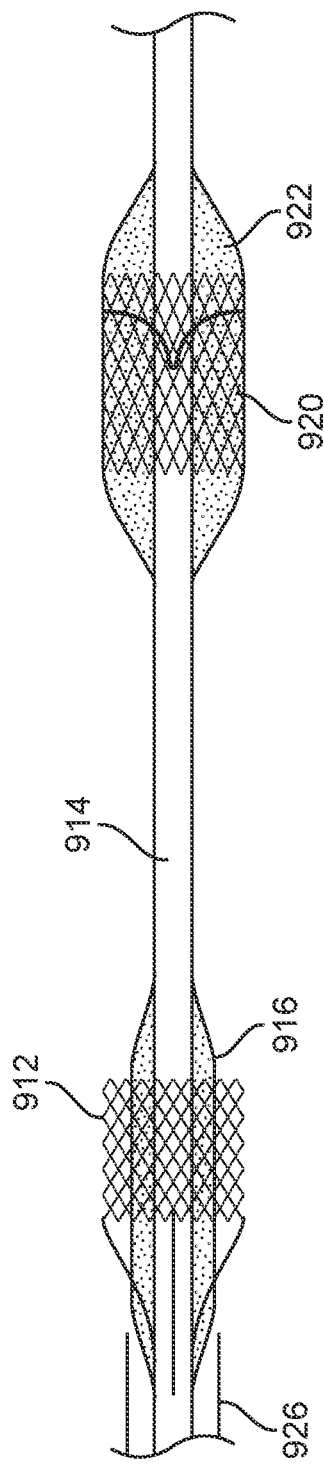
Figure 9D:
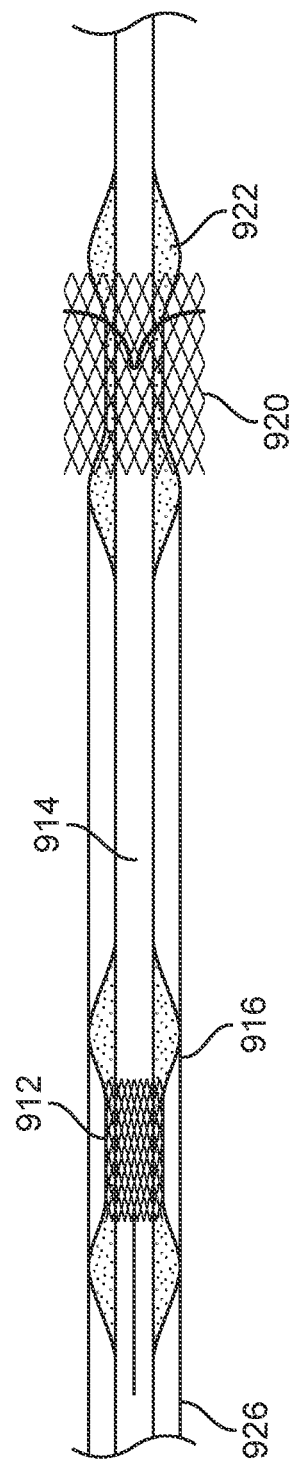

FIGS. 9A-9D show an eighth embodiment of an embolic filter 912 in accordance with the present invention where both a prosthetic valve 920 and a filter 912 are balloon expandable. The embolic filter 912 is mounted on a proximal-most balloon 916 of a double-balloon catheter 914. A balloon-expandable prosthetic valve 920, such as an Edwards Lifesciences Sapien® valve, is mounted on a distal-most balloon 922 on the catheter 914. Both the prosthetic valve 920 and the embolic filter 912 are thus deployed by balloon, where the balloons are configured to be inflated and deflated separately. As shown in FIG. 9A, prior to deployment, the prosthetic valve 912 and the embolic filter 920 are crimped onto balloons 916 and 922, respectively. As shown in FIG. 9B, the filter 912 is deployed by inflation of balloon 916. The filter 920 is then deployed by inflating balloon 922 (FIG. 9C), 922 is deflated once the filter has been deployed. While filter 912 remains expanded After valve deployment, balloon 922 is deflated, and a sheath 926 (previously used for deploying the valve delivery system) is advanced to collapse the filter 912 to allow removal of the system.

Figure 10:
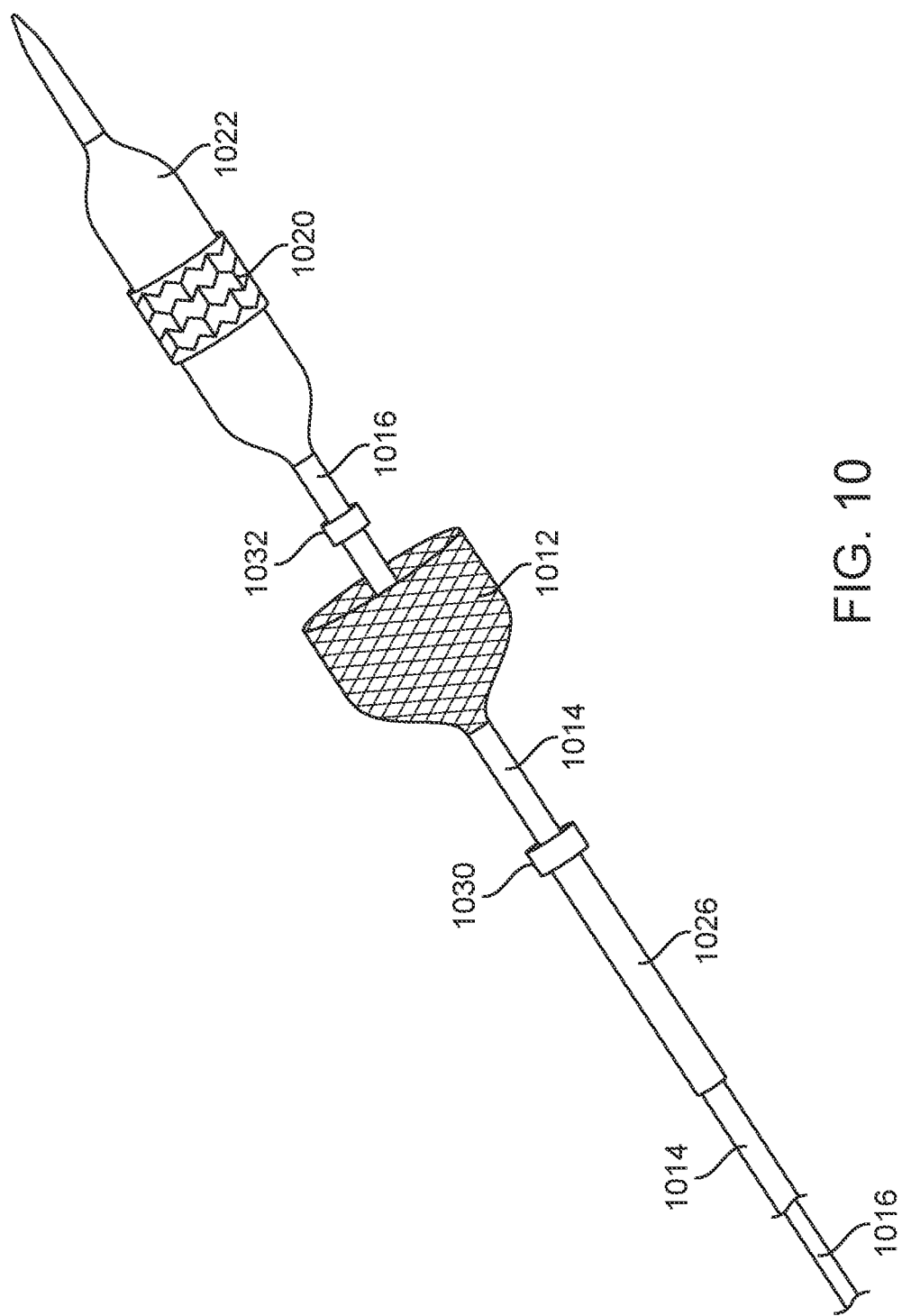
FIG. 10 shows a ninth embodiment of a valve delivery system according to the present invention similar to that of FIG. 1 where the embolic filter comprises a self-supporting mesh basket with no additional support frame.

FIG. 10 shows a ninth embodiment of an embolic filter 1012 in accordance with the present invention. The embolic filter 1012 is a self-supporting mesh basket with no additional support frame. It is deployed and retrieved by the retraction and advancement of a constraining sheath 1026 that is part of the delivery system of a balloon-expandable valve 1020, such as an Edwards Lifesciences Sapien® valve. In this example, the embolic filter 1012 is deployed via a self-expanding mechanism, while the prosthetic valve 1020 is deployed via the inflation of a deployment balloon 1022. The filter 1012 may be mounted on a separate filter deployment catheter 1014, which is deployed over the balloon catheter 1016 but inside the constraining sheath 1026. This configuration allows the balloon catheter 1016 to be advanced and withdrawn independent of the filter deployment catheter 1014 and related mechanism. The embolic filter 1012 may be deployed either by retraction of the constraining sheath 1026, or advancement of the catheter 1014, to release the embolic filter from the constraining sheath. After filter deployment, the prosthetic valve 1020 is deployed by inflation of the deployment balloon 1022. After the valve 1020 has been deployed, the deployment balloon 1022 is deflated, and the embolic filter 1012 is collapsed either by withdrawing the embolic filter into the constraining sheath 1026 or by advancing the constraining sheath over the embolic filter. The may further comprise a downstream or proximal stop 1030 on a shaft of the catheter 1014 which limits proximal movement of the filter 1012 (when configured to slide on the shaft) on the shaft and an upstream or distal stop 1032 which limits distal movement of the filter on the shaft.

The embolic filter may be a mesh or other filter structure made of knitted, woven or nonwoven fibers, filaments or wires that will have a pore size chosen to allow blood to pass through but prevent emboli above a certain size from passing through. The embolic filter may also consist of a non-woven sheet, such as a thin sheet of polymer or metal, that has been perforated with holes of a single size or different sizes. The embolic filter material may be made of a metal, a polymer or a combination thereof and may optionally have an antithrombogenic coating on its surface. The embolic filter may also consist of some combination of a perforated sheet and a fiber-based mesh or other filter material or other filter structure. The embolic filter may consist of a single layer or multiple layers of any of the above configurations to increase the filtering efficiency and reduce the effective pore size.

The embolic protection device is delivered in an undeployed or retracted condition. A tubular outer delivery sheath may be used to maintain the embolic protection device in the undeployed condition. (FIG. 2A-2D). The delivery catheter may optionally include a shoulder or stop positioned proximal to the embolic protection device to maintain the position of the embolic protection device on the catheter as the delivery sheath is withdrawn during deployment. Alternatively, a pusher catheter that fits in between the catheter and the delivery sheath may be used to facilitate deployment such as the filter deployment catheter in FIG. 10.

Alternatively, the filter may be deployed via the inflation of balloon inside the filter, which may be cylindrically or conically shaped, or otherwise shaped to match the geometry of the filter. Such a filter may be retrieved by withdrawing it into a retrieval sheath (FIG. 9).

Another alternative delivery mechanism is to reduce the effective length of the embolic filter with a member attached to either the distal or proximal end (or both). In an embolic filter with a design such as shown in FIGS. 2A-2D, compressing the filter lengthwise will result in expansion of the diameter of the filter structure and resultant deployment of the filter. During retrieval, the filter may be elongated to reduce its diameter and collapse the filter. This can be accomplished with two independent filter deployment catheters that can be independently advanced or retracted to effect the change in length.

The catheter may be configured as a diagnostic catheter, a guiding catheter or therapeutic catheter. A specific example would be the delivery system for a transcatheter aortic valve.

The embolic filter will typically have at least one open end and define one or more internal collection regions which receive and capture emboli entering with blood flow through the open end. In other configurations, the embolic filter may have two open ends, for example having a cylindrical configuration which allows blood to flow in one end and out from the other end.

In many embodiments, the filter membranes will be self-supporting in the deployed condition. By self-supporting it is meant that the filter membrane can be deployed without further support into a three-dimensional configuration that maintains sufficient contact with the vessel wall to form an adequate seal to prevent emboli above a certain size from passing around the outside of the embolic protection device. In one example, the embolic filter can be constructed of a resilient mesh or other filter material that can be compressed into the undeployed condition and will self-expand into the deployed condition. Such structures are described in U.S. Pat. No. 9,877,821, previously incorporated herein by reference.

In another example, the embolic filter may comprise a filter membrane, matrix, or the like and a separate supporting structure. The filter membrane may comprise any known structure for filtering emboli from blood, including meshes, perforated sheets, porous sheets, fibrous structures, and the like, or any combinations thereof. The filter membrane can be resilient, slack, plastically deformable, or combinations thereof.

The supporting structure may be located externally to the filter membrane, internally within the filter membrane, or both eternally and internally. For example, the supporting structure may comprise a framework that includes one or more longitudinal struts or hoops that are attached to or otherwise engage the filter membrane to hold the filter membrane in its opened or deployed configuration with the aorta or other target blood vessel. The hoops and/or struts may be formed of a resilient metal, polymer, or other material to provide a self-expanding framework that assumes a low profile or narrow configuration when constrained by a sheath for delivery and which assumes an expanded or deployed configuration when released from constraint. Alternatively, the framework or other support structure may comprise a malleable or plastically deformable material to provide expansion by applying a radial outward force to an interior of the support structure, typically using an inflatable balloon or other expansion mechanism.

Hybrid constructions that combine features of the self-supporting structure and the frame-supported structure may also be used. Hybrid deployment methods, such as balloon-assisted self-expansion or longitudinal compression of the support structure can also be utilized.

The support structures and the filter membranes of the embolic filters will often have the same lengths, but embolic filter may also be constructed with the embolic filter membrane being longer or shorter than the supporting structure. Specific relative longitudinal dimensions of the filter membranes of the embolic filters may be as shown in the drawings. In another alternate construction, the support structure and/or filter membrane can be conical with and enlarged or base end of the cone being positioned on the upstream side.

The embolic filter can be retracted and withdrawn with the catheter after the diagnostic or interventional procedure has been completed. Optionally, the embolic filter may include features to assist in retracting the device for retrieval from the patient's aorta. For example, a conical guiding structure may be slidably attached to the catheter at the proximal end of the device, the purpose of which is to assist the embolic filter in collapsing when a retrieval sheath is advanced along the conical guiding structure. In another example, portions of the embolic filter may be constructed with retraction members that are configured like purse strings or lassos around the circumference of the device. A pull loop or other graspable structure near the downstream end of the embolic filter is connected to the retraction members by one or more connecting members. In one preferred embodiment, the embolic filter is configured to close its upstream end first to assure that any captured emboli do not migrate out of the filter during retrieval. This can be accomplished by providing one or more pull loops for selectively retracting different sections of the device. The retraction members and connecting members may be made of suture, wire, plastic filament or a combination of these materials. In an alternate construction, the "Stent" Support Structure described above may also be configured to serve as the retraction members.

The embolic filter may be fixedly attached to the catheter or attached via a slidable attachment, or some combination of the two. A sliding attachment can consist of one or more rings, roller bearings or other structures that allow the embolic protection device to slide freely on the catheter. The sliding attachment will preferably have a low coefficient of friction and/or a lubricious coating so that movement of a catheter through the sliding attachment will not jostle or dislodge the embolic protection device. Alternatively, the sliding attachment can contain an additional sealing element, such as resilient flaps, an iris structure, or an expandable sealing material.

The overall undeployed diameter of the embolic filter as collapsed for delivery (including the diameter of its constraining sheath) preferably will be no larger than the largest section of the catheter (such as the collapsed diameter of a prosthetic valve, including its constraining sheath), which is most likely in the distal section of the catheter. In the case of a valve delivery system, the catheter is typically reduced in size proximal to the valve, which would potentially allow the integration of an embolic filter and its constraining member without changing the overall tracking profile of the valve delivery system.

The embolic filter is in an undeployed condition on the catheter as it is inserted into a patient's aorta. The embolic filter is ideally deployed in the ascending aorta prior to the ostia of the cerebral arteries. Optionally, a delivery sheath may be used to hold the embolic filter in the undeployed position. The embolic filter can also be constrained for delivery by crimping it onto a balloon catheter, or by elongating its support structure to reduce its diameter.

The entire embolic filter or a portion of it may be coated with an anti-thrombogenic coating, for example a bonded heparin coating, to reduce the formation of clots that could become potential emboli. Alternatively, or in addition, the embolic filter or a portion of it may have a drug-eluting coating containing an anti-inflammatory or anti-stenosis agent. The embolic filter of the present invention can also be used for embolic protection of other organ systems. For example, an embolic filter can be deployed in the patient's descending aorta for preventing embolic particles in the aortic blood flow from entering the renal arteries and embolizing in the patient's kidneys.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A prosthetic heart valve delivery catheter having integrated embolic protection, said catheter comprising:
    a catheter shaft having a distal portion;
    an expandable balloon on the distal portion of the catheter shaft;
    a prosthetic valve disposed on the expandable balloon on the distal portion of the catheter shaft; and
    an embolic filter disposed on the distal portion of the shaft at a location proximal of the prosthetic valve, said embolic filter having a collapsed configuration and a deployed configuration wherein an outer periphery of the filter is configured to contact a blood vessel wall;
    wherein the embolic filter comprises a cylindrical wall having an open distal end unattached to the shaft and a closed proximal end sealing coupled to the catheter shaft, wherein a proximal region of the cylindrical wall is movably everted and allows the open distal end to axially translate relative to the catheter shaft while the closed proximal end remains stationary relative to the catheter shaft.

2. The catheter of claim 1, wherein the closed proximal end is fixed to the catheter shaft.

3. The catheter of claim 1, wherein the closed proximal end is slidably coupled to the catheter shaft.

4. The catheter of claim 1, wherein at least the distal portion of the cylindrical wall is self-expanding.

5. The catheter of claim 1, wherein at least the distal portion of the cylindrical wall comprises a self-expanding filter.

* * * * *